(12) United States Patent
Schmid et al.

(10) Patent No.: US 6,927,240 B2
(45) Date of Patent: Aug. 9, 2005

(54) GRANULAR SOLID WITH MONODISPERSE PARTICLE SIZE DISTRIBUTION

(75) Inventors: Karl Heinz Schmid, Mettmann (DE); Gerhard Wollmann, Hilden (DE); Bernhard Gutsche, Hilden (DE); Michael Neuss, Cologne (DE); Gilbert Roegel, Nanteuil les Meaux (FR)

(73) Assignee: Cognis Deutschland GmbH & Co. KG, Duesseldorf (DE)

(*) Notice: Subject to any disclaimer, the term of this patent is extended or adjusted under 35 U.S.C. 154(b) by 215 days.

(21) Appl. No.: 10/220,787

(22) PCT Filed: Feb. 21, 2001

(86) PCT No.: PCT/EP01/01927
§ 371 (c)(1),
(2), (4) Date: Dec. 13, 2002

(87) PCT Pub. No.: WO01/64326
PCT Pub. Date: Sep. 7, 2001

(65) Prior Publication Data
US 2003/0113354 A1 Jun. 19, 2003

(30) Foreign Application Priority Data
Mar. 2, 2000 (DE) .......................... 100 09 996

(51) Int. Cl.[7] .................. A01N 25/00; A61N 47/00; B29G 9/00
(52) U.S. Cl. .................. 514/772; 264/9; 264/12; 264/13
(58) Field of Search .................. 514/772; 264/9, 264/12, 13

(56) References Cited

U.S. PATENT DOCUMENTS

| | | |
|---|---|---|
| 1,985,424 A | 12/1934 | Piggott |
| 2,016,962 A | 10/1935 | Flint et al. |
| 2,703,798 A | 3/1955 | Schwartz |
| 4,172,887 A | 10/1979 | Vanlerberghe et al. |
| 5,374,716 A | 12/1994 | Biermann et al. |
| 5,464,874 A * | 11/1995 | Balzer .................. 514/777 |
| 5,576,425 A | 11/1996 | Hill et al. |
| 5,622,656 A * | 4/1997 | Huc et al. .................. 264/4.7 |
| 5,674,504 A | 10/1997 | Kauffmann |
| 5,705,169 A | 1/1998 | Stein et al. |
| 5,730,960 A | 3/1998 | Stein et al. |
| 5,840,943 A | 11/1998 | Ansmann et al. |
| 5,945,091 A | 8/1999 | Habeck et al. |
| 6,193,960 B1 | 2/2001 | Metzger et al. |

FOREIGN PATENT DOCUMENTS

| | | |
|---|---|---|
| DE | 1 165 574 | 8/1960 |
| DE | 27 25 924 | 12/1978 |
| DE | 30 35 331 | 4/1982 |
| DE | 197 12 033 | 9/1998 |
| DE | 197 56 377 | 6/1999 |
| EP | 0 301 298 | 2/1989 |
| EP | 0 693 471 | 1/1996 |
| EP | 0 694 521 | 1/1996 |
| EP | 0 818 450 | 1/1998 |
| FR | 2 252 840 | 11/1974 |
| GB | 962 919 | 8/1960 |
| WO | WO 90/03977 | 4/1990 |
| WO | WO 92/06984 | 4/1992 |
| WO | WO 95/34528 | 12/1995 |
| WO | WO 99/33555 | 7/1999 |

OTHER PUBLICATIONS

Heike Kelkenberg, "Detergenzien auf Zuckerbasis", Tenside Surfactants Detergents 25, 1988, pp. 8–13.
J. Falbe, "Surfactants in Consumer Products", Springer Verlag, Berlin, 1987, pp. 54–125.
J. Falbe et al., "Katalysatoren, Tenside und Mineraloladditive", Thieme Verlag.Stuttgart, 1978, pp. 123–217.
R. Lochhead et al., "Encyclopedia of Polymers and Thickeners for Cosmetics", Cosmetics and Toiletries vol. 108, May 1993 pp. 95–135.
C. Todd et al."Volatile silicone fluids for cosmetic formulations", Cosmetics and Toiletries vol. 91, Jan. 1976, pp 29–32.
P. Finkel, "Formulierung kosmetischer Sonnenschutzmittel", SÖFW–Journal, 122 Jahrgang, Aug. 1996, pp 543–546, 548.
P. Finkel, "Formulierung kosmetischer Sonnenschutzmittel", Parfumerie und Kosmetik, 80, Jahrgang, Nr. Mar. 1999, pp 10–12, 14–16.
"Kosmetische Farbemittel" of the Farbstoffkommission der Deutschen Forschungsgemeinschaft, Verlag Chemie, Weinheim, 1984, pp 81–106.

* cited by examiner

Primary Examiner—Stephen J. Lechert, Jr.
(74) Attorney, Agent, or Firm—Arthur G. Seifert

(57) ABSTRACT

A process for making granular solids involving: (a) providing a substantially anhydrous preparation, which is solid at room temperature and contain at least one cosmetic feed material; (b) liquifying the substantially anhydrous preparation to form a melt; (c) providing a vibrating casting plate used for droplet formation; (d) introducing the melt onto the vibrating casting plate to form melt droplets thereon; (e) providing a cooling medium; and (f) contacting the melt droplets with the cooling medium which is passed countercurrently to the melt droplets, thus forming the granular solids, and wherein the granular solids have a monodisperse particle size distribution and are substantially free of particles having a diameter of less than 0.3 mm.

21 Claims, No Drawings

GRANULAR SOLID WITH MONODISPERSE PARTICLE SIZE DISTRIBUTION

This application is a 371 of PCT/EP01/01927 filed Feb. 21, 2001.

BACKGROUND OF THE INVENTION

FIELD OF THE INVENTION

The invention is in the field of cosmetics and relates to readily soluble solids with a monodisperse particle size distribution, to a process for their preparation, and to their use for the preparation of surface-active preparations, specifically compositions for haircare and bodycare.

The formulation of cosmetic feed materials which are solid at room temperature, such as, for example, emulsifiers, wax bodies or bodying agents, is usually carried out by spray crystallization. Usually, a number of material pressure nozzles, so-called solid-cone nozzles, are installed in the top of the spray towers, via which the feed materials are atomized into the spray tower. In this process, the stream exiting from the nozzle with high turbulence ruptures after just a short distance from the mouth of the nozzle and forms droplets, the rupturing being additionally intensified by the rotation of the stream. The crystallization product prepared in this way has a broad particle size spectrum. Because of the size content which is produced during this operation and the risk of a dust explosion, spraying plants of this type are subject to increased obligations regarding procedures in case of accident, which includes not inconsiderable requirements for operational safety and leads to increased costs for the preparation process. A further problem consists in the tendency of the spray crystals to cake together, which considerably increases the expenditure during incorporation into the end formulations.

Amongst the producers of cosmetic raw materials, there is therefore lively interest in solids with a narrowed particle size spectrum, in particular with a negligible fines or dust content (<0.5 mm) of less than 1% by weight. At the same time, the desire is for products which dissolve more rapidly in an oily or aqueous phase and thus can be incorporated more easily.

The object of the present invention was therefore to provide novel granular solids which are free from the described disadvantages, i.e. have a monodisperse particle size distribution, virtually no dust content and an improved dissolution rate both in an aqueous and an oily medium.

DESCRIPTION OF THE INVENTION

The invention provides granular solids with a monodisperse particle size distribution which are obtainable by liquefying a predominantly anhydrous preparation which is solid at room temperature and which comprises at least one cosmetic feed material, making a stream of the melt into droplets using a casting plate by vibration, and passing a cooling medium countercurrently to the droplets, which causes them to solidify.

Surprisingly, it has been found that the aim set can be achieved by means of droplet generation which is different from conventional spray crystallization. Here, the feed mixtures are introduced as melt into the drop-formation tower via a perforated plate or a die plate. As a result of an excited membrane, a frequency is impressed onto the liquid, the liquid thread is interrupted again and again and, due to the interfacial tension, small spheres form which then pass into the actual spraying tower and then, as they fall freely through, for example, a countercurrent stream of dehydrated cold air, are crystallized. Depending on the perforation diameter and membrane oscillation frequency, it is possible to set a defined particle spectrum without dust fraction. A plant of this type is thus no longer subject to the increased obligations regarding procedures in case of accident, which leads to a drastic reduction in the technical expenditure and the costs associated therewith. In addition, in the production of the granules there is usually a broad solidification range. The products frequently have one phase in the form of supercooled liquids, meaning that post-crystallization is associated with a heat of reaction. This can prevent block formation by the particles sticking together. Finally, an essential advantage consists in the fact that the "beads" obtained in this way have a significantly improved solubility, compared with conventional supply forms, for example pellets or flakes, both in oily and aqueous media. Moreover, this substantiates the claim that the substances are novel.

The invention further relates to a process for the preparation of granular solids with a monodisperse particle size distribution, in which a predominantly anhydrous preparation which is solid at room temperature and which comprises at least one cosmetic feed material is liquefied, a stream of the melt is made into droplets using a casting plate by vibration and a cooling medium is passed countercurrently to the droplets, which causes them to solidify.

Cosmetic Ingredients

The choice of cosmetic ingredients is unimportant in itself provided they are in the form of solids in anhydrous form at temperatures below 25° C., preferably at 18 to 22° C. Suitable ingredients are preferably emulsifiers, wax bodies and bodying agents, and mixtures thereof. These are usually used as anhydrous preparations, melted and then formed into drops. It is, however, also possible to use preparations which are predominantly anhydrous, i.e. in which the water fraction is less than 50% by weight, preferably less than 25% by weight and in particular less than 5% by weight. This is the case, for example, when anionic or nonionic emulsifiers are used which are often in the form of aqueous surfactant pastes as a result of the preparation.

Emulsifiers

Suitable emulsifiers are, for example, nonionogenic surfactants from at least one of the following groups:

alkyl and/or alkenyl oligoglycosides, fatty acid N-alkylpolyhydroxyalkylamides;

addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and alkylamines having 8 to 22 carbon atoms in the alkyl radical;

addition products of from 1 to 15 mol of ethylene oxide onto castor oil and/or hydrogenated castor oil;

addition products of from 15 to 60 mol of ethylene oxide onto castor oil and/or hydrogenated castor oil;

mixed ethers and ethoxylated fatty acid alkyl esters;

partial esters of glycerol and/or sorbitan with unsaturated, linear or saturated, branched fatty acids having 12 to 22 carbon atoms and/or hydroxycarboxylic acids having 3 to 18 carbon atoms, and adducts thereof having 1 to 30 mol of ethylene oxide;

partial esters of polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and adducts thereof having 1 to 30 mol of ethylene oxide;

mixed esters of pentaerythritol, fatty acids, citric acid and fatty alcohol according to German Patent 1165574 and/or mixed esters of fatty acids having 6 to 22 carbon atoms, methyl glucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers or corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols and glycerol carbonate.

Alkyl and alkenyl oligoglycosides are known nonionic surfactants which conform to the formula (I)

$$R^1O\text{-}[G]_p \quad (I)$$

in which $R^1$ is an alkyl and/or alkenyl radical having 4 to 22 carbon atoms, G is a sugar radical having 5 or 6 carbon atoms and p is a number from 1 to 10. They can be obtained by appropriate processes of preparative organic chemistry. As representative for the extensive literature, reference may be made here to the specifications EP-A1 0301298 and WO 90/03977. The alkyl and/or alkenyl oligoglycosides can be derived from aldoses or ketoses having 5 or 6 carbon atoms, preferably from glucose. The preferred alkyl and/or alkenyl oligoglycosides are thus alkyl and/or alkenyl oligoglucosides. The index number p in the general formula (I) gives the degree of oligomerization (DP), i.e. the distribution of mono- and oligoglycosides and is a number between 1 and 10. While p in a given compound must always be an integer and can here primarily assume the values p=1 to 6, the value p for a certain alkyl oligoglycoside is an analytically determined calculated parameter which is in most cases a fraction. Preference is given to using alkyl and/or alkenyl oligoglycosides having an average degree of oligomerization p of from 1.1 to 3.0. From a performance viewpoint, preference is given to those alkyl and/or alkenyl oligoglycosides whose degree of oligomerization is less than 1.7 and is in particular between 1.2 and 1.4. The alkyl or alkenyl radical $R^1$ can be derived from primary alcohols having 4 to 11, preferably 8 to 10 carbon atoms. Typical examples are butanol, caproic alcohol, caprylic alcohol, capric alcohol and undecyl alcohol, and technical-grade mixtures thereof, as are obtained, for example, in the hydrogenation of technical-grade fatty acid methyl esters or in the course of the hydrogenation of aldehydes from the Roelen oxo synthesis. Preference is given to alkyl oligoglucosides of chain length $C_8$–$C_{10}$ (DP=1 to 3) which are produced as forerunnings during the distillative separation of technical-grade $C_8$–$C_{18}$-coconut fatty alcohol and may be contaminated with a content of less than 6% by weight of $C_{12}$-alcohol, and also alkyl oligoglucosides based on technical-grade $C_{9/11}$-oxo alcohols (DP=1 to 3). The alkyl or alkenyl radical $R^1$ can also be derived from primary alcohols having 12 to 22, preferably 12 to 14, carbon atoms. Typical examples are lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol, and technical-grade mixtures thereof which can be obtained as described above. Preference is given to alkyl oligoglucosides based on linear or branched fatty alcohols having 8 8 to 18 or 16 to 18 or carbon atoms, in particular technical-grade coconut fatty alcohol or cetearyl alcohol or isostearyl alcohol.

Fatty acid N-alkylpolyhydroxyalkylamides are likewise suitable nonionic emulsifiers which preferably conform to the formula (II)

$$R^2CO\text{—}\underset{\underset{R^3}{|}}{N}\text{—}[Z] \quad (II)$$

in which $R^2CO$ is an aliphatic acyl radical having 6 to 22 carbon atoms, $R^3$ is an alkyl or hydroxyalkyl radical having 1 to 4 carbon atoms and [Z] is a linear or branched polyhydroxyalkyl radical having 3 to 12 carbon atoms and 3 to 10 hydroxyl groups. The fatty acid N-alkylpolyhydroxyalkylamides are known substances which can usually be obtained by a reductive amination of a reducing sugar with an alkylamine or an alkanolamine and subsequent acylation with a fatty acid, a fatty acid alkyl ester or a fatty acid chloride. With regard to processes for their preparation, reference is made to the U.S. Pat. Nos. 1,985,424, 2,016,962 and 2,703,798, and the international patent application WO 92/06984. A review of this topic is given by H. Kelkenberg in Tens.Surf. Deterg. 25, 8 (1988). The fatty acid N-alkylpolyhydroxyalkylamides are preferably derived from reducing sugars having 5 or 6 carbon atoms, in particular from glucose. The preferred fatty acid N-alkylpolyhydroxyalkylamides are thus fatty acid N-alkylglucamides, as given by the formula (III):

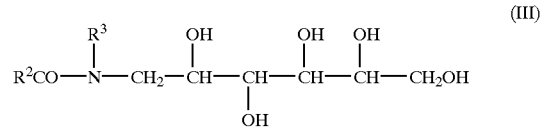

$$R^2CO\text{—}\underset{\underset{R^3}{|}}{N}\text{—}CH_2\text{—}CH\text{—}\underset{\underset{OH}{|}}{CH}\text{—}\underset{\underset{OH}{|}}{CH}\text{—}\underset{\underset{OH}{|}}{CH}\text{—}CH_2OH \quad (III)$$

As fatty acid N-alkylpolyhydroxyalkylamides, preference is given to using glucamides of the formula (III) in which $R^3$ is an alkyl group and $R^2CO$ is the acyl radical of caproic acid, caprylic acid, capric acid, lauric acid, myristic acid, palmitic acid, palmoleic acid, stearic acid, isostearic acid, oleic acid, elaidic acid, petroselic acid, linoleic acid, linolenic acid, arachidic acid, gadoleic acid, behenic acid or erucic acid or technical-grade mixtures thereof. Particular preference is given to fatty acid N-alkylglucamides of the formula (III) which are obtained by reductive animation of glucose with methylamine and subsequent acylation of palmitic, stearic and/or isostearic acid or a corresponding derivative. In addition, the polyhydroxyalkylamides can also be derived from maltose and palatinose.

The addition products of ethylene oxide and/or of propylene oxide onto fatty alcohols, fatty acids, alkylphenols or onto castor oil are known, commercially available products. These are homolog mixtures whose average degree of alkoxylation corresponds to the ratio of the quantitative amounts of ethylene oxide and/or propylene oxide and substrate with which the addition reaction is carried out. These are preferably addition products of from 5 to 50 and in particular 10 to 20 mol of ethylene oxide onto fatty alcohols having 12 to 22 and preferably 16 to 18 carbon atoms.

Typical examples of suitable ethoxylated partial glycerides are addition products of from 1 to 30, preferably 5 to 10, mol of ethylene oxide onto hydroxystearic acid monoglyceride, hydroxystearic acid diglyceride, isostearic acid monoglyceride, isostearic acid diglyceride, oleic acid monoglyceride, ricinoleic acid moglyceride, ricinoleic acid diglyceride, linoleic acid monoglyceride, linoleic acid diglyceride, linolenic acid monoglyceride, linolenic acid diglyceride, erucic acid monoglyceide, erucic acid diglyceride, tartaric acid monoglyceride, tartaric acid diglyceride, citric acid monoglyceride, citric acid diglyceride, malic acid monoglyceride, malic acid diglyceride, and technical-grade mixtures thereof, which may also comprise to a minor degree small amounts of triglyceride from the preparation process.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Also suitable are addition products of from 1 to 30, preferably 5 to 10, mol of ethylene oxide onto said sorbitan esters.

Typical examples of suitable polyglycerol esters are the polyol poly-12-hydroxystearates. These are known substances which are described, for example, in the international patent application WO 95/34528 (Henkel). The polyol component of the emulsifiers can be derived from substances which have at least two, preferably 3 to 12 and in particular 3 to 8, hydroxyl groups and 2 to 12 carbon atoms. Typical examples are:

(a) glycerol and polyglycerol;
(b) alkylene glycols, such as, for example, ethylene glycol, diethylene glycol, propylene glycol;
(c) methyol compounds, such as, in particular, trimethylolethane, trimethylolpropane, trimethylolbutane, pentaerythritol and dipentaerythritol;
(d) alkyl oligoglucosides having 1 to 22, preferably 1 to 8 and in particular 1 to 4, carbon atoms in the alkyl radical, such as, for example, methyl glucoside and butyl glucoside;
(e) sugar alcohols having 5 to 12 carbon atoms, such as, for example, sorbitol or mannitol,
(f) sugars having 5 to 12 carbon atoms, such as, for example, glucose or sucrose;
(g) amino sugars, such as, for example, glucamine.

Among the emulsifiers to be used according to the invention, reaction products based on polyglycerol are of particular importance due to their excellent performance properties. It has proven particularly advantageous to use selected polyglycerols which have the following homolog distribution (the preferred ranges are given in brackets):

| Glycerol | 5 to 35 (15 to 30) | % by weight |
|---|---|---|
| Diglycerols | 15 to 40 (20 to 32) | % by weight |
| Triglycerols | 10 to 35 (15 to 25) | % by weight |
| Tetraglycerols | 5 to 20 (8 to 15) | % by weight |
| Pentaglycerols | 2 to 10 (3 to 8) | % by weight |
| Oligoglycerols | ad 100 | % by weight |

Further suitable polyglycerol esters are polyglycerol-3-diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (polyglycerol caprate T2010/90), polyglyceryl-3 cetyl ether (Chimexane® NL), polyglyceryl-3 distearate (Cremophor® GS 32) and polyglyceryl polyricinoleate (Admul® WOL 1403) polyglyceryl dimerate isostearate, and mixtures thereof. Examples of further suitable polyol esters are the mono-, di- and triesters of trimethylolpropane or pentaerythritol with lauric acid, coconut fatty acid, tallow fatty acid, palmitic acid, stearic acid, oleic acid, behenic acid and the like, which have optionally been reacted with 1 to 30 mol of ethylene oxide.

Suitable nonionic emulsifiers are, in particular, also mixed ethers or hydroxy mixed ethers, which are reaction products of the fatty alcohol polyglycol ethers already given with $C_1$–$C_8$ alkyl halides or $C_8$–$C_{12}$ epoxides. Also suitable are alkoxylated fatty acid lower alkyl esters which are obtained by, for example, inserting 1 to 10 mol of ethylene oxide into the ester bond of $C_{12}$–$C_{18}$-fatty acid methyl esters. This is possible, inter alia, by reacting the esters with ethylene oxide in the presence of calcined hydrotalcites as catalysts.

It is also possible to use zwitterionic surfactants as emulsifiers. The term "zwitterionic surfactants" is used to refer to those surface-active compounds which carry, in the molecule, at least one quaternary ammonium group and at least one carboxylate group and one sulfonate group. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having 8 to 18 carbon atoms in the alkyl or acyl group, and cocoacylaminoethyl hydroxyethylcarboxymethyl glycinate. Particular preference is given to the fatty acid amide derivative known under the CTFA name *Cocamidopropyl Betaine*. Likewise suitable emulsifiers are ampholytic surfactants. Ampholytic surfactants are to be understood as meaning those surface-active compounds which, apart from containing a $C_{8/18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each having about 8 to 18 carbon atoms in the alkyl group. Particularly preferred ampholytic surfactants are N-cocoalkylaminopropionate, cocoacylaminoethylaminopropionate and $C_{12/18}$ acylsarcosine. Finally, cationic surfactants are also suitable as emulsifiers, those of the ester quat type, preferably methyl-quaternized difatty acid triethanolamine ester salts, being particularly preferred.

Wax Bodies

Typical examples of suitable wax bodies which can be made into drops for the purposes of the invention are, for example, natural waxes, such as, for example, candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin wax (wool wax), uropygial grease, ceresine, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example esters of fatty acids with fatty alcohols, polyalkylene waxes and polyethylene glycol waxes in question.

In addition to the fats, suitable additives are also fat-like substances, such as lecithins and phospholipids. The term lecithins is understood by the person skilled in the art as meaning those glycerophospholipids which form from fatty acids, glycerol, phosphoric acid and choline by esterification. In the specialist field, lecithins are therefore also often referred to as phosphatidylcholines (PC). Examples of natural lecithins which may be mentioned are cephalins, which are also referred to as phosphatidic acids and are derivatives of 1,2-diacyl-sn-glycerol-3-phosphoric acids. By contrast, the term "phospholipids" usually means mono- and, preferably, diesters of phosphoric acid with glycerol (glycerol phosphates) which are generally considered to be fats. In addition, sphingosines and sphingolipids are also suitable.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polyhydric, optionally hydroxy-substituted, carboxylic acids with fatty alcohols having 6 to 22 carbon atoms, specifically long-chain esters of tartaric acid; fatty substances, such as, for example, fatty ketones, fatty aldehydes, fatty ethers and fatty carbonates which have, in total, at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying Agents

The most important group of bodying agents which can be formed into drops are the fatty alcohols. These are to be understood as meaning primary aliphatic alcohols which preferably conform to the formula (IV)

$$R^4OH \quad (IV)$$

in which $R^4$ is an aliphatic, linear or branched hydrocarbon radical having 6 to 22 carbon atoms and 0 and/or 1, 2 or 3 double bonds. Typical examples are caproic alcohol, caprylic alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoleyl alcohol, linolenyl alcohol, eleostearyl alcohol, arachyl alcohol, gadoleyl alcohol, behenyl alcohol, erucyl alcohol and brassidyl alcohol, and technical-grade mixtures thereof which are produced, for example, during the high-pressure hydrogenation of technical-grade methyl esters based on fats and oils or aldehydes from the Roelen oxosynthesis, and as monomer fraction in the dimerization of unsaturated fatty alcohols. Preference is given to technical-grade linear and/or branched fatty alcohols having 16 to 18 carbon atoms, such as, for example cetearyl alcohol or isostearyl alcohol.

Further suitable bodying agents are partial glycerides, i.e. monoglycerides, diglycerides and technical-grade mixtures thereof are also suitable as additives and may, as a result of the preparation, also comprise small amounts of triglycerides. The partial glycerides preferably conform to the formula (V)

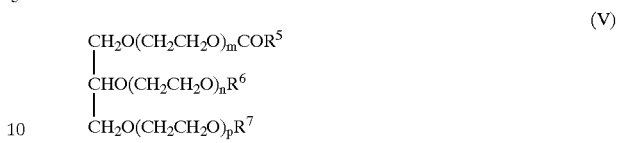

in which $R^5CO$ is a linear or branched, saturated and/or unsaturated acyl radical having 6 to 22, preferably 12 to 18, carbon atoms, $R^6$ and $R^7$, independently of one another, are $R^5CO$ or OH and the sum (m+n+p) is 0 or numbers from 1 to 100, preferably 5 to 25, with the proviso that at least one of the two radicals $R^6$ and $R^7$ is OH. Typical examples are mono- and/or diglycerides based on caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselic acid, linoleic acid, linolenic acid, eleostearic acid, arachidic acid, gadoleic acid, behenic acid and erucic acid, and technical-grade mixtures thereof. Preference is given to using technical-grade cetearyl glycerides, palmitic acid glycerides, stearic acid glycerides and/or isostearic acid glycerides which have a monoglyceride content in the range from 50 to 95% by weight, preferably 60 to 90% by weight.

Special Mixtures

In a preferred embodiment of the present invention, sugar surfactants of the alkyl oligoglucoside type are used together with bodying agents from the group of fatty alcohols where it is advisable to use representatives which have identical alkyl radicals since these not only have performance advantages, but are also of interest economically since they are already produced as intermediates during the synthesis of the glucosides. Drops are very particularly preferably made from those mixtures which comprise alkyl oligoglucosides of the formula (I) and fatty alcohols of the formula (IV) in which $R^1$ and $R^4$ are linear or branched alkyl radicals having 16 to 18 carbon atoms, specifically cetearyl or isostearyl radicals in the weight ratio 10:90 to 90:10 and specifically 40:60 to 60:40. The glucoside/fatty alcohol ratio can be adjusted, for example, through the choice of fatty alcohol excess in the acetalation. Subsequently, fatty alcohol can be removed by, for example, extraction in the near-critical range or molecular distillation. Such products, even when in nongranular form, are available commercially, for example under the names Emulgade® PL 68/50 or Montanov® 68.

In a further preferred embodiment, drops are made from mixtures which comprises alkyl oligoglucosides of the formula (I) in which $R^1$ is a linear or branched alkyl radical having 8 to 18 carbon atoms, and polyglycerol poly-12-hydroxystearates in the weight ratio 40:60 to 60:40 and in particular 50:50. Such products, even when in nongranular form, are available commercially under the name Eumulgin® VL 75.

Drop Formation

The drop formation carried out for the purposes of the process of the invention using a vibrating casting plate with excited membrane is already known for the processing of resins and low-viscosity polyesters. Appropriate components are sold, for example, by Rieter-Automatik under the name "Droppo Line" for use in textile technology. For the purposes of the process of the invention, preference is given to those casting plates which consist of a heatable upper and lower plate. The lower plate is usually in the form of a perforated disk, through whose openings or channels or capillary nozzles or dropping tubes the drops then pass into the spraying tower. In a particular embodiment of the process, the nozzles are designed so that, as well as the starting material stream, they also permit the feed of an additional stream of gas ("control air"), with which the droplets can be further nebulized. This stream of gas can be preheated, for example to 100 to 120° C., meaning that any traces of water still present in the starting material are evaporated with its help. The capacity of perforated disks which usually have 10 to 750 bores may preferably be in the range from 0.3 to 3 kg/h/bore, the diameter of the bores is between 0.25 and 1.4 mm. Here, granules are obtained which have a diameter of from 1.6 to 2.7 times the diameter of the bores.

The oscillation frequency of the perforated plates ("dropping plates") is typically in the range from 100 to 10 000 and preferably 200 to 800 Hz. It can be generated via an excited membrane, an oscillating plunger, a vibrating plate or sonic excitation.

A further advantage over conventional processes is also that it is possible to work at a pressure which is only slightly above atmospheric pressure (typically: 100 to 4 000 mbar). The temperature with which the feed materials are conveyed into the dropping tower is limited by the solidification range and is usually in the range from 40 to 100° C., where it must be ensured that the starting materials are not overheated since this may lead to decomposition and caking. Feed temperatures which are 3 to 10° C. above the solidification point of the feed materials have proven particularly effective. The starting materials usually have a viscosity of less than 500 mPas (Brookfield, spindle 1, 20° C., 10 rpm). The drops fall downward perpendicularly in areas of low turbulence in the tower. The probability of two or more drops meeting and caking together to form a so-called "raspberry granule" is low. Although in principle cooling can take place with a cold liquid, for practical reasons cooling in the dropping tower using cold air in countercurrent is advisable, as is adequately described in the prior art. The granules are almost spherical and, depending on the orifices in the perforated plate and the frequency, have average diameters in the range from 1 to 2.5 mm. If desired, the spraying tower can be equipped with a shaking-screen floor in order to make the particle size distribution even more homogeneous.

The dust fraction, e.g. particles with particle sizes of less than 0.3 mm is virtually zero in this process, and therefore no apparatuses are required to separate off the dust from the exit air. In the absence of dust, a circulatory gas procedure is possible, which leads to a reduction in dehumidification expenditure for introduced fresh air. Instead of air, because of the circulatory gas procedure, it is of course also possible to use inert gas.

For products with residual heat and with aftercrystallization heat, an aftercooling section may be connected downstream of the dropping tower. Examples of suitable aftercoolers are gas-permeated fluidized, fixed or sliding beds, liquid-cooled helical conveyors, pneumatic conveyors or aftercooling belts. For products which firstly form a supercooled liquid prior to solidification, the crystallization may be stimulated by adding inert nucleating agents to the melt or into the gaseous stream, forcing a secondary stream into the nozzle (rotational flow), dropping the drops through a sonar field, e.g. low-frequency or an ultrasound field or the known generation of satellite drops by changing the frequency.

Industrial Applicability

The invention further provides for the use of the granular solids for preparing surface-active, primarily cosmetic, preparations, in particular for the field of skincare and haircare compositions. They can, however, also be used for the field of oral and dental hygiene, and for laundry detergents, dishwashing detergents, cleaners and hand modifiers. The use amount of the granules is in the range from 1 to 70% by weight, preferably 5 to 50% by weight and in particular 15 to 35% by weight, based on the compositions.

These compositions can also comprise, as further auxiliaries and additives, mild surfactants, oily bodies, thickeners, superfatting agents, stabilizers, polymers, silicone compounds, fats, waxes, lecithins, phospholipids, biogenic active ingredients, UV light protection factors, antioxidants, deodorants, antiperspirants, antidandruff agents, film formers, swelling agents, insect repellents, self-tanning agents, tyrosine inhibitors (depigmentation agents), hydrotropes, solubilizers, preservatives, perfume oils, dyes and the like. In a particular embodiment of the invention, it is also possible that the additives described here and below in more detail can be made into drops together with the cosmetic ingredients and then be used as a "compound" mixture. This applies in particular to UV light protection filters, antioxidants and biogenic active ingredients, where it is also a criterion here again that the additives should as far as possible be solid at room temperature.

Surfactants

Surface-active substances which may be present are anionic, nonionic, cationic and/or amphoteric or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefinsulfonates, alkyl ether sulfonates, glyceryl ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular vegetable products based on wheat) and alkyl (ether) phosphates. If the anionic surfactants contain polyglycol ether chains, these may have a conventional homolog distribution, but preferably have a narrowed homolog distribution. Typical examples of nonionic surfactants are fatty alcohol polyglycol ethers, alkylphenol polyglycol ether, fatty acid polyglycol esters, fatty acid amide polyglycol ethers, fatty amine polyglycol ethers, alkoxylated triglycerides, mixed ethers or mixed formals, or glucoronic acid derivatives, protein hydrolyzates (in particular vegetable products based on wheat), polyol fatty acid esters, sugar esters, sorbitan esters, polysorbates and amine oxides. If the nonionic surfactants contain polyglycol ether chains, these may have a conventional homolog distribution, but preferably have a narrowed homolog distribution. Typical examples of cationic surfactants are quaternary ammonium compounds, such as, for example, dimethyldistearylammonium chloride and ester quats, in particular quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. Said surfactants are all known compounds. With regard to the structure and the preparation of the substances, reference may be made to the relevant review papers, for example J. Falbe (ed.), "Surfactants in Consumer Products" Springer Verlag, Berlin, 1987, p. 54–124 or J. Falbe (ed.), "Katalysatoren, Tenside und Mineralöladditive", Thieme Verlag, Stuttgart, 1978, p. 123–217. Typical examples of particularly suitable mild, i.e. particularly skin-compatible, surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, these last preferably being based on wheat proteins.

Oily Bodies

Suitable oily bodies are, for example, Guerbet alcohols based on fatty alcohols having 6 to 18, preferably 8 to 10, carbon atoms, esters of linear $C_6$–$C_{22}$-fatty acids with linear $C_6$–$C_{22}$-fatty alcohols, esters of branched $C_6$–$C_{13}$-carboxylic acids with linear $C_6$–$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$–$C_{22}$-fatty acids with branched alcohols, in particular 2-ethylhexanol, esters of $C_{18}$–$C_{38}$-alkylhydroxy carboxylic acids with linear or branched $C_6$–$C_{22}$-fatty alcohols (cf. DE 19756377 A1), in particular dioctyl malate, esters of linear and/or branched fatty acids with polyhydric alcohols (such as e.g. propylene glycol, dimerdiol or trimertriol) and/or Guerbet alcohols, triglycerides based on $C_6$–$C_{10}$-fatty acids, liquid mono-/di-/triglyceride mixtures based on $C_6$–$C_{18}$-fatty acids, esters of $C_6$–$C_{22}$-fatty alcohols and/or Guerbet alcohols with aromatic carboxylic acids, in particular benzoic acid, esters of $C_2$–$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$–$C_{22}$-fatty alcohol carbonates, such as, for example, dicaprylyl carbonate, Guerbet carbonates, esters of benzoic acid with linear and/or branched $C_6$–$C_{22}$-alcohols (e.g. Finsolv® TN), linear or branched, symmetrical or asymmetrical dialkyl ethers having 6 to 22 carbon atoms per alkyl group, such as, for example, dicaprylyl ether, ring-opening products of epoxidized fatty acid esters with polyols, silicone oils (cyclomethicone, silicon methicon grades etc.) and/or aliphatic or naphthenic hydrocarbons, such as, for example, such as squalane, squalene or dialkylcyclohexanes under consideration.

Thickeners

Suitable thickeners are hydroxy fatty alcohols having 12 to 22, and preferably 16 to 18, carbon atoms and also fatty acids or hydroxy fatty acids. Suitable thickeners are, for example, Aerosil grades (hydrophilic silicas), polysaccharides, in particular xanthan gum, guar-guar, agar-agar, alginates and Tyloses, carboxymethylcellulose and hydroxyethylcellulose, and also relatively high molecular weight polyethylene glycol mono- and diesters of fatty acids, polyacrylates, (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, such as, for example, ethoxylated fatty acid glycerides, esters of fatty acids with polyols, such as, for example, pentaerythritol or trimethylolpropane, fatty alcohol ethoxylates with narrowed homolog distribution or alkyl oligoglucosides, and electrolytes such as sodium chloride and ammonium chloride.

Superfatting Agents

Superfatting agents which can be used are substances such as, for example, lanolin and lecithin, and polyethoxylated or acylated lanolin and lecithin derivatives, polyol fatty acid esters, monoglycerides and fatty acid alkanolamides, these last also serving as foam stabilizers.

Stabilizers

Stabilizers which can be used are metal salts of fatty acids, such as, for example, the stearates or ricinoleates of magnesium, aluminum and/or zinc.

Polymers

Suitable cationic polymers are, for example, cationic cellulose derivatives, such as, for example, a quaternized hydroxyethylcellulose which is available under the name Polymer JR 400® from Amerchol, cationic starch, copolymers of diallylammonium salts and acrylamides, quaternized vinylpyrrolidone/vinyl-imidazole polymers, such as, for example, Luviquat® (BASF), condensation products of polyglycols and amines, quaternized collagen polypeptides, such as, for example, lauryldimonium hydroxypropyl hydrolyzed collagen (Lamequat®L/Grünau), quaternized wheat polypeptides, polyethyleneimine, cationic silicone polymers, such as, for example, amodimethicones, copolymers of adipic acid and dimethylamino hydroxypropyldiethylenetriamine (Cartaretine®/Sandoz), copolymers of acrylic acid with dimethyldiallylammonium chloride (Merquat® 550/Chemviron), polyaminopolyamides, as described, for example, in FR 2252840 A, and crosslined water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bisdimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octylacrylamide/methyl methacrylate/tert-butylaminoethyl methacrylate/2-hydroxypropylmethacrylate copolymers, polyvinylpyrrolidone, vinylpyrrolidone/vinyl acetate copolymers, vinylpyrrolidone/dimethylaminoethyl methacrylate/vinylcaprolactam terpolymers, and optionally derivatized cellulose ethers and silicones. Further suitable polymers and thickeners are listed in Cosmetics & Toiletries 108, 95 [1993].

Suitable silicone compounds are, for example, dimethylpolysiloxanes, methylphenylpolysiloxanes, cyclic silicones and amino-, fatty-acid-, alcohol-, polyether-, epoxy-, fluorine-, glycoside- and/or alkyl-modified silicone compounds which can either be liquid or in resin form at room temperature. Also suitable are simethicones, which are mixtures of dimethicones having an average chain length of from 200 to 300 dimethylsiloxane units and hydrogenated silicates. A detailed review of suitable volatile silicones can additionally be found in Todd et al. in Cosm. Toil. 91, 27 (1976).

UV Light Protection Filters and Antioxidants

The term "UV light protection factors" means, for example, organic substances (light protection filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

3-benzylidenecamphor or 3-benzylidenenorcamphor and derivatives thereof, e.g. 3-(4-methylbenzylidene)-camphor, as described in EP 0693471 B1;

4-aminobenzoic acid derivatives, preferably 2-ethylhexyl 4-(dimethylamino)benzoate, 2-octyl 4-(dimethylamino)benzoate and amyl 4-(dimethylamino)-benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3, 3-phenyl-cinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methyl-benzophenone, 2,2'-dihydroxy-4-methoxybenzophenone;

esters of benzalmalonic acid, preferably di-2-ethyl-hexyl 4-methoxybenzalmalonate;

triazine derivatives, such as, for example, 2,4,6-trianilino (p-carbo-2'-ethyl-1'-hexyloxy)-1,3,5-triazine and octyltriazone, as described in EP 0818450 A1 or dioctylbutamidotriazone (Uvasorb® HEB);

propane-1,3-diones, such as, for example, 1-(4-tert-butylphenyl)-3-(4'-methoxyphenyl)propane-1,3-dione;

ketotricyclo(5.2.1.0)decane derivatives, as described in EP 0694521 B1.

Suitable water-soluble substances are:

2-phenylbenzimidazole-5-sulfonic acid and the alkali metal, alkaline earth metal, ammonium, alkylammonium, alkanolammonium and glucammonium salts thereof;

sulfonic acid derivatives of benzophenones, preferably 2-hydroxy-4-methoxybenzophenone-5-sulfonic acid and its salts;

sulfonic acid derivatives of 3-benzylidenecamphor, such as, for example, 4-(2-oxo-3-bornylidenemethyl)-benzenesulfonic acid and 2-methyl-5-(2-oxo-3-bornylidene)sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in DE 19712033 A1 (BASF). The UV-A and UV-B filters can of course also be used in mixtures. As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminum and cerium, and mixtures thereof. Salts which may be used are silicates (talc), barium sulfate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide. Further suitable UV light protection filters are given in the review by P. Finkel in S ÖFW-Journal 122, 543 (1996) and Parfümerie und Kosmetik 3 (1999), page 11ff.

As well as the two abovementioned groups of primary light protection substances, it is also possible to use secondary light protection agents of the antioxidant type; these interrupt the photochemical reaction chain which is triggered when WV radiation penetrates the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Biogenic Active Ingredients

The term "biogenic active ingredients" means, for example, tocopherol, tocopherol acetate, tocopherol palmitate, ascorbic acid, (deoxy)ribonucleic acid, and fragments thereof, retinol, bisabolol, allantoin, phytantriol, panthenol, AHA acids, amino acids, ceramides, pseudoceramides, essential oils, plant extracts and vitamin complexes.

Deodorants and Antimicrobial Agents

Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT, Henkel KGaA, Düsseldorf/FRG). The substances inhibit enzyme activity, thereby reducing the formation of odor. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", such as, for example, extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise the following ingredients:

astringent active ingredients,
oil components,
nonionic emulsifiers,
coemulsifiers,
bodying agents,
auxiliaries, such as, for example, thickeners or complexing agents and/or
nonaqueous solvents, such as, for example, ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be:

- anti-inflammatory, skin-protective or perfumed essential oils,
- synthetic skin-protective active ingredients and/or
- oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Antidandruff Active Ingredients

Suitable antidandruff active ingredients are piroctone olamine (1-hydroxy-4-methyl-6-(2,4,4-trimythylpentyl)-2-(1H))-pyridinone monoethanolamine salt), Baypival® (climbazole), ketoconazole® (4-acetyl-1-{4-[2-(2,4-dichlorophenyl)r-2-(1H-imidazol-1-ylmethyl)-1,3-dioxylanc-4-ylmethoxyphenyl}piperazine, selenium disulfide, colloidal sulfur, sulfur polyethylene glycol sorbitan monooleate, sulfur ricinol polyethoxylate, sulfur tar distillate, salicylic acid (or in combination with hexachlorophene), undexylenic acid monoethanolamide-sulfosuccinate Na salt, Lamepon® UD (protein undecylenic acid condensate), zinc pyrithione, aluminum pyrithione and magnesium pyrithione/dipyrithione magnesium sulfate.

Swelling Agents

The swelling agents for aqueous phases may be montmorillonites, clay mineral substances, Pemulen, and alkyl-modified Carbopol grades (Goodrich). Other suitable polymers and swelling agents are given in the review by R. Lochhead in Corm. Toil. 108, 95 (1993).

Insect Repellents

Suitable insect repellents are N,N-diethyl-m-toluamide, 1,2-pentanediol or ethyl butylacetylaminopropionate.

Self-tanning Agents and Depigmentation Agents

A suitable self-tanning agent is dihydroxyacetone. Suitable tyrosine inhibitors, which prevent the formation of melanin and are used in depigmentation compositions, are, for example, arbutin, kojic acid, coumaric acid and ascorbic acid (vitamin C).

Hydrotropic Agents

To improve the flow behavior, it is furthermore possible to use hydrotropic agents, such as, for example, ethanol, isopropyl alcohol or polyols. Polyols which are suitable here preferably have 2 to 15 carbon atoms and at least two hydroxyl groups. The polyols can also contain further functional groups, in particular amino groups, or can be modified with nitrogen. Typical examples are

- glycerol;
- alkylene glycols, such as, for example, ethylene glycol, diethylene glycol, propylene glycol, butylene glycol, hexylene glycol, and polyethylene glycols having an average molecular weight of from 100 to 1 000 daltons;
- technical-grade oligoglycerol mixtures having a degree of self-condensation of from 1.5 to 10, such as, for example, technical-grade diglycerol mixtures having a diglycerol content of from 40 to 50% by weight;
- methylol compounds, such as, in particular, trimethylolethane, trimethylolpropane, trimethylolbutane, pentaerythritol and dipentaerythritol;
- lower alkyl glucosides, in particular those having 1 to 8 carbon atoms in the alkyl radical, such as, for example, methyl and butyl glucoside;
- sugar alcohols having 5 to 12 carbon atoms, such as, for example, sorbitol or mannitol;
- sugars having 5 to 12 carbon atoms, such as, for example, glucose or sucrose;
- aminosugars, such as, for example, glucamine;
- dialcohol amines, such as diethanolamine or 2-amino-1, 3-propanediol.

Preservatives

Suitable preservatives are, for example, phenoxy-ethanol, formaldehyde solution, parabens, pentanediol or sorbic acid, and the other classes of substance listed in Annex 6, Part A and B of the Cosmetics Directive.

Perfume Oils

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethol, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Essential oils, of relatively low volatility, which are mostly used as aroma components, are also suitable as perfume oils, e.g. sage oil, camomile oil, oil of cloves, melissa oil, mint oil, cinnamon leaf oil, linden blossom oil, juniperberry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilllat, irotyl and floramat alone or in mixtures.

Dyes

Dyes which can be used are the substances which are approved and suitable for cosmetic purposes, as are listed, for example, in the publication "Kosmetische Färbemittel" [Cosmetic Colorants] from the Farbstoffkommission der Deutschen Forschungsgemeinschaft [Dyes Commission of the German Research Council], Verlag Chemie, Weinheim, 1984, pp. 81–106. These dyes are normally used in concentrations of from 0.001 to 0.1% by weight, based on the total mixture.

EXAMPLES

Example 1

In a Droppo-Line unit from Rieter Automatik GmbH with 0.3 mm nozzles, a 50:50 mixture of cetearyl oligoglucoside and cetearyl alcohol (Emulgade® PL 68/50, Cognis Deutschland GmbH, melting point 640° C.) was made into drops at a rate of 0.7 kg/h/perforation. Starting from a melting temperature of 800° C., a product temperature of 21° C. was established. Cooling took place with cold air at 3° C. from a falling height of 11 m. Dust-free flowable granules were obtained; these consisted of uniform beads, >70% of which had a size of 0.6 mm. A product compressed with 780 kg/m$^2$ could, after a storage period of 2 h, be divided again into individual beads without problems. The product showed no temperature increase as a result of residual heat. The dissolution rate in hexyl laurate of the beads obtained in this way was tested as follows in comparison with a commercial product in the form of prills: in each case 900 g of hexyl laurate were heated to 60° C.; in this oil were dissolved, with stirring, amounts of 100 g in each case of the beads according to the invention and, for comparison, the commercially available flakes. The dissolution rates determined were 8 min for the beads according to the invention and 21 min for the conventional flaked product.

Example 2

In a Droppo-Line unit from Rieter Automatik GmbH with 0.5 mm nozzles, a 50:50 mixture of cetearyl oligoglucoside and cetearyl alcohol (Emulgade® PL 68/50) was made into drops at a rate of 2.5 kg/h/perforation. Starting from a melting temperature of 80° C., a product temperature of 55° C. was established. Cooling was carried out using cold air at 10° C. from a falling height of 11 m. Dust-free flowable granules were obtained; these consisted of uniform beads, >70% of which had a size of 0.95 mm. A product compressed with 780 kg/m$^2$ could, after a storage period of 2 h, be divided again into individual beads without problems. The product did not exhibit any increase in temperature as a result of residual heat. The dissolution rates in hexyl laurate determined were 9 min for the beads according to the invention and 21 min for the conventional flaked product.

Example 3

In a Droppo-Line unit from Rieter Automatik GmbH with 0.5 mm nozzles, a 50:50 mixture of cocoalkyl oligoglucoside and polyglycerol poly-12-hydroxystearate (Emulgin® VL 75, Cognis Deutschland GmbH) was made into drops at a rate of 1.1 kg/h/perforation. Starting from a temperature of 95° C., a product temperature of 65° C. was established. Cooling took place using cold air at 3° C. from a falling height of 11 m. Dust-free flowable granules were obtained which consisted of uniform beads, >70% of which had a size of 0.95 mm.

Example 4

In a Droppo-Line unit from Rieter Automatik GmbH with 0.5 mm nozzles, a cetearyl alcohol (Lanette® O, Cognis Deutschland GmbH, melting point 51° C.) was made into drops at a rate of 2.5 kg/h/perforation. Starting from a melting temperature of 65° C., a product temperature of 39° C. was established. Cooling was carried out with cold air at 10° C. from a falling height of 11 m. Dust-free flowable granules were obtained; these consisted of uniform beads, >70% of which had a size of 1 mm. A product compressed with 780 kg/m$^2$ could, after a storage period of 2 h, be divided again into individual beads without problems. The product did not exhibit any increase in temperature as a result of residual heat. The dissolution rates in hexyl laurate determined were 6 min for the beads according to the invention and 12 min for the conventional flaked product.

Example 5

In a Droppo-Line unit from Rieter Automatik GmbH with 0.3 mm nozzles, a glycerol monostearate (Cutina® GMS-V, Cognis Deutschland GmbH, melting point 59° C.) was made into drops at a rate of 2.0 kg/h/perforation. Starting from a melting temperature of 7° C., a product temperature of 38° C. was established. Cooling took place with cold air at 3° C. from a falling height of 11 m. Dust-free flowable granules were obtained; these consisted of uniform beads, >70% of which had a size of 0.65 mm. The dissolution rates determined were 8 min for the beads according to the invention and 19 min for the conventional flaked product.

Example 6

In a Droppo-Line unit from Rieter Automatik GmbH with 0.3 mm nozzles, a mixture (melting temperature 62° C.) of (a) 100 parts of a 50:50 mixture of cetearyl oligoglucoside and cetearyl alcohol (Emulgade® PL 68/50), (b) 5 parts of sodium cetyl/stearyl sulfate (Lanette® E, Cognis Deutschland GmbH) and (c) 40 parts of glycerol monostearate (Cutina® GMS-V) were made into drops at a rate of 1.5 kg/h/perforation. Starting from a melting temperature of 75° C., a product temperature of 43° C. was established. Cooling took place with cold air at 10° C. from a falling height of 11 m. Dust-free flowable granules were obtained; these consisted of uniform beads, >70% of which had a size of 0.65 mm. The dissolution rates determined were 21 min for the beads according to the invention and 41 min for the conventional flaked product.

Example 7

In a Droppo-Line unit from Rieter Automatik GmbH with 0.5 mm nozzles, a mixture (melting temperature 62° C.) of (a) 100 parts of a 50:50 mixture of cetearyl oligoglucoside and cetearyl alcohol (Emulgade® PL 68/50) and 10 parts of wheat protein hydrolyzate powder (Gluadin® WP, Cognis Deutschland GmbH) was made into drops at a rate of 1.5 kg/h/perforation. Starting from a melting temperature of 75° C., a product temperature of 46° C. was established. Cooling was carried out with cold air at 10° C. from a falling height of 11 m. Dust-free flowable granules were obtained; these consisted of uniform beads, >70% of which had a size of 0.95 mm. The dissolution rates determined were 10 min for the beads according to the invention and 21 min for the conventional flaked product.

Example 8

In a Droppo-Line unit from Rieter Automatik GmbH with 0.3 mm nozzles, a mixture (melting temperature 52° C.) of (a) 80 parts of Cutina® CBS (mixture of bodying waxes, Cognis Deutschland GmbH) (b) 15 parts of ceteareth-12 (Eumulgin® B 1, Cognis Deutschland GmbH) and (c) 15 parts of ceteareth-20 (Eumulgin® B 2, Cognis Deutschland GmbH) was made into drops at a rate of 1.5 kg/h/perforation. Starting from a melting temperature of 65° C., a product temperature of 38° C. was established. Cooling was carried out with cold air at 10° C. from a falling height of 11 m. Dust-free flowable granules were obtained; these consisted of uniform beads, >70% of which had a size of 0.6 mm. The dissolution rates determined were 16 min for the beads according to the invention and 29 min for the conventional flaked product.

Example 9

In a Droppo-Line unit from Rieter Automatik GmbH with 0.3 mm nozzles, a mixture (melting temperature 55° C.) of 80 parts of steanc acid mono/diglyceride (Cutina® MD, Cognis Deutschland GmbH), (b) 8 parts of ceteareth-12 (Eumulgin B 1) and (c) parts of ceteareth-20 (Eumulgin® B 2) were made into drops at a rate of 1.5 kg/h/perforation. Starting from a melting temperature of 70° C., a product temperature of 45° C. was established. Cooling took place with cold air at 10° C. from a falling height of 11 m. Dust-free flowable granules were obtained; these consisted of uniform beads, >70% of which had a size of 0.6 mm. The dissolution rates determined were 14 min for the beads according to the invention and 26 min for the conventional flaked product.

Example 10

In a Droppo-Line unit from Rieter Automatik GmbH with 0.5 mm nozzles, a mixture (melting temperature 56° C.) of 30 parts of cetearyl alcohol (Lanette® O), (b) 40 parts of glycerol monostearate (Cutina® GMS-V) and (c) 8 parts of ceteareth-20 (Eumulgin® B 2) was made into drops at a rate of 1.8 kg/h/perforation. Starting from a melting temperature of 65° C., a product temperature of 39° C. was established. Cooling took place with cold air at 10° C. from a falling height of 11 m. Dust-free flowable granules were obtained; these consisted of uniform beads, >70% of which had a size of 1 mm. The dissolution rates determined were 8 min for the beads according to the invention and 15 min for the conventional flaked product.

Example 11

In a Droppo-Line unit from Rieter Automatik GmbH with 0.3 mm nozzles, a mixture (melting temperature 48° C.) of (a) 20 parts of stearic/palmitic acid (Cutina® FS 45, Cognis Deutschland GmbH), (b) 40 parts of Cutina® CBS (mixture of bodying waxes) and (c) 10 parts of 4-methylbenzylidenecamphor (Eusolex® 6300, Merck) was made into drops at a rate of 1.1 kg/h/perforation. Starting from a melting temperature of 60° C., a product temperature of 31° C. was established. Cooling was carried out with cold air at 10° C. from a falling height of 11 m. Dust-free flowable granules were obtained; these consisted of uniform beads, >70% of which had a size of 0.6 mm. The dissolution rates determined were 18 min for the beads according to the invention and 37 min for the conventional flaked product.

Example 12

In a Droppo-Line unit from Rieter Automatik GmbH with 0.3 mm nozzles, a mixture (melting temperature 48° C.) of (a) 40 parts of cetearyl alcohol (Lanette® O) and (b) 10 parts of benzophenone-3 (NeoHeliopan® BB, Haarmann & Reimer) was made into drops at a rate of 1.5 kg/h/perforation. Starting from a melting temperature of 60° C., a product temperature of 34° C. was established. Cooling was carried out with cold air at 10° C. from a falling height of 11 m. Dust-free flowable granules were obtained; these consisted of uniform beads, >70% of which had a size of 0.6 mm. The dissolution rates determined were 9 minutes for the beads according to the invention and 16 min for the conventional flaked product.

Example 13

In a Droppo-Line unit from Rieter Automatik GmbH with 0.3 mm nozzles, a mixture (melting temperature 56° C.) of (a) 40 parts of glycerol monostearate (Cutina® GMS-V) and (b) parts of benzophenone-3 (NeoHeliopan® BB) was made into drops at a rate of 1.5 kg/h/perforation. Starting from a melting temperature of 70° C., a product temperature of 41° C. was established. Cooling was carried out with cold air at 10° C. from a falling height of 11 m. Dust-free flowable granules were obtained; these consisted of uniform beads, >70% of which had a size of 0.6 mm. The dissolution rates determined were 10 min for the beads according to the invention and 18 min for the conventionally flaked product.

Example 14

In a Droppo-Line unit from Rieter Automatik GmbH with 0.3 mm nozzles, a mixture (melting temperature 51° C.) of (a) 45 parts of cetearyl alcohol (Lanette® O) and (b) 10 parts of carotene was made into drops at a rate of 1.3 kg/h/perforation. Starting from a melting temperature of 67° C., a product temperature of 38° C. was established. Cooling was carried out with cold air at 10° C. from a falling height of 11 m. Dust-free flowable granules were obtained; these consisted of uniform beads, >70% of which had a size of 0.6 mm. The dissolution rates determined were 5 min for the beads according to the invention and 11 min for the conventionally flaked product.

Example 15

In a Droppo-Line unit from Rieter Automatik GmbH with 0.3 mm nozzles, a mixture (melting temperature 53° C.) of (a) 45 parts of cetearyl alcohol (Lanette® O) and (b) 7 parts of sodium cocoalkyl sulfate (Sulfopon® 1218, Cognis Deutschland GmbH, 65% by weight of active substance) was made into drops at a rate of 1.0 kg/h/perforation (for this purpose, the melt was dispersed using a homogenizer (Supraton) and passed to the spraying tower). Starting from a melting temperature of 70° C., a product temperature of 41° C. was established. Cooling was carried out with cold air at 10° C. from a falling height of 11 m. Dust-free flowable granules were obtained; these consisted of uniform beads, >70% of which had a size of 0.6 mm. The dissolution rates determined were 7 min for the beads according to the invention and 13 min for the conventional flaked product.

Example 16

In a Droppo-Line unit from Rieter Automatik GmbH with 0.3 mm nozzles, a mixture (melting temperature 53° C.) of (a) 50 parts of cetearyl alcohol (Lanette® O) and (b) 4 parts of potassium cetyl phosphate (25% by weight of active substance) was made into drops at a rate of 1.1 kg/h/perforation (for this purpose, the melt was dispersed by means of a homogenizer (Supraton) and passed to the spraying tower). Starting from a melting temperature of 70° C., a product temperature of 42° C. was established. Cooling was carried out with cold air at 10° C. from a falling height of 11 m. Dust-free flowable granules were obtained; these consisted of uniform beads, >70% of which had a size of 0.6 mm. The dissolution rates determined were 8 min for the beads according to the invention and 15 min for the conventional flaked product.

Example 17

In a Droppo-Line unit from Rieter Automatik GmbH with 0.3 mm nozzles, a mixture (melting temperature 80° C.) of (a) 70 parts of a technical-grade cocoalkyl polyglucoside mixture consisting of 80% by weight of glucoside and 20% by weight of fatty alcohol), and 30 parts of a paste consisting of 50% by weight of cocoalkyl polyglucoside and 50% by weight of water (Plantacare® APG 1200, Cognis Deutschland GmbH) was made into drops at a rate of 0.80 kg/h/perforation (for this purpose, the melt was dispersed using a homogenizer (Supraton) and passed to the spraying tower). The mixture was fed into the drop-formation spray head at a temperature of 95° C. Cooling in the spraying tower with a falling height of 11 m took place with cold air at 10° C. Dust-free flowable granules were obtained; these consisted of uniform beads, >70% of which had a size of 0.6 mm. The dissolution rate of the resulting beads was tested as follows in comparison with a corresponding product in flaked form: in each case 100 g of the pearl or flaked product were heated, with stirring, at 50° C. in 1 liter of water, the beads requiring only half of the time to dissolve which was necessary for dissolution of the flaked product.

Example 18

In a Droppo-Line unit from Rieter Automatik GmbH with 0.3 mm nozzles, a mixture of (a) 70 parts of $C_{12/18}$-fatty alcohol+20EO and (b) 30 parts of a paste consisting of 50% by weight of cocoalkyl polyglucoside and 50% by weight of water (Plantacare® APG 1200) was made into drops at a rate of 0.90 kg/h/perforation (for this purpose, the melt was dispersed using a homogenizer (Supraton) and passed to the spraying tower). The mixture was fed into the drop-formation spray head at a temperature of 95° C. Cooling in the spraying tower with a falling height of 11 m took place with cold air at 10° C. Dust-free flowable granules were obtained; these consisted of uniform beads, >70% of which had a size of 0.6 mm. A product compressed with 500 kg/m² could, after a storage period of 2 h, be divided again into individual beads without problems. The product did not exhibit any increase in temperature as a result of residual heat. The dissolution rate of the resulting beads was tested as follows in comparison with a corresponding product in flaked form: in each case 100 g of the bead or flaked product were heated, with stirring, at 30° C. in 1 liter of water, the beads only requiring half of the time to dissolve which was necessary for dissolution of the flaked product.

Example 19

In a Droppo-Line unit from Rieter Automatik GmbH with 0.3 mm nozzles, a mixture (melting temperature 80° C.) of (a) 50 parts of a technical-grade cocoalkyl polyglucoside mixture consisting of 80% by weight of glucoside and 20% by weight of fatty alcohol), and 50 parts of $C_{12/18}$-fatty alcohol+20EO decyl ether was made into drops at a rate of 0.80 kg/h/perforation (for this purpose, the melt was dispersed using a homogenizer (Supraton) and passed to the spraying tower). The mixture was fed into the drop-formation spraying head at a temperature of 90° C. Cooling in the spraying tower with a falling height of 11 m was carried out with cold air at 10° C. Dust-free flowable granules were obtained; these consisted of uniform beads, >70% of which had a size of 0.6 mm. The dissolution rate of the resulting beads was tested as follows in comparison with a corresponding product in flaked form: in each case 100 g of the bead or flaked product were heated, with stirring, at 50° C. in 1 liter of water, the beads requiring only half of the time to dissolve which was necessary for dissolution of the flaked product.

Example 20

In a Droppo-Line unit from Rieter Automatik GmbH with 0.3 mm nozzles, stearic acid+40EO methyl ester (melting temperature 51° C.) was made into drops at a rate of 0.7 kg/h/perforation. Starting from a melting temperature of 65° C., a product temperature of 24° C. was established. Cooling took place with cold air at 5° C. from a falling height of 11 m. Dust-free flowable granules were obtained; these consisted of uniform beads, >70% of which had a size of 0.6 mm. The dissolution rate of the resulting beads was tested as follows in comparison with a corresponding product in flaked form: in each case 100 g of the bead or flaked product were heated, with stirring, at 50° C. in 1 liter of water, the beads requiring only half of the time to dissolve which was necessary for the dissolution of the flaked product.

Example 21

In a Droppo-Line unit from Rieter Automatik GmbH with 0.5 mm nozzles, a mixture (melting temperature 45° C.) of (a) 50 parts of coconut fatty acid +10EO methyl ester and (b) 50 parts of polyethylene glycol (molecular weight 4 000) was made into drops at a rate of 1.7 kg/h/perforation. Starting from a melting temperature of 75° C., a product temperature of 34° C. was established. Cooling took place with cold air at 15° C. from a falling height of 11 m. The resulting drops were then powdered in silica. Dust-free flowable granules were obtained; these consisted of uniform beads, >70% of which had a size of 1 mm. The dissolution rate of the resulting beads was tested as follows in comparison with a corresponding product in flaked form: in each case 100 g of the bead or flaked product were heated, with stirring, at 50° C. in 1 liter of water, the beads requiring only half of the time to dissolve which was necessary for the dissolution of the flaked product.

What is claimed is:

1. A process for making granular solids comprising:
   (a) providing a substantially anhydrous preparation, which is solid at room temperature and contains at least one cosmetic feed material;
   (b) liquifying the substantially anhydrous preparation to form a melt;
   (c) providing a vibrating casting plate used for droplet formation;
   (d) introducing the melt onto the vibrating casting plate to form melt droplets thereon;
   (e) providing a cooling medium; and
   (f) contacting the melt droplets with the cooling medium which is passed countercurrently to the melt droplets, thus forming the granular solids, and wherein the granular solids have a monodisperse particle size distribution and are substantially free of particles having a diameter of less than 0.3 mm.

2. The process of claim 1 wherein the cosmetic feed material is selected from the group consisting of an emulsifier, a wax body, a bodying agent, and mixtures thereof.

3. The process of claim 1 wherein the substantially anhydrous preparation contains less than about 50% by weight water, based on the weight of the preparation.

4. The process of claim 1 wherein the substantially anhydrous preparation contains a mixture of an alkyl polyglycoside and a fatty alcohol, both having identical alkyl radicals.

5. The process of claim 1 wherein the vibrating casting plate vibrates at an oscillating frequency ranging from about 100 to 1000 Hz.

6. The process of claim 1 wherein the melt drops are contacted with the cooling medium in a drop-formation tower.

7. The process of claim 1 wherein the granular solids have a dust content of less than 1% by weight, based on the weight of the granular solids.

8. The product of the process of claim 2.

9. The product of the process of claim 4.

10. A cosmetic composition containing from about 1 to 70% by weight of the granular solids of claim 1.

11. A process for making granular solids comprising:
(a) providing a substantially anhydrous preparation, which is solid at room temperature and contains at least one cosmetic feed material selected from the group consisting of one or more emulsifiers, wax bodies, and bodying agents, and mixtures thereof;
(b) liquifying the substantially anhydrous preparation to form a melt;
(c) providing a vibrating casting plate used for droplet formation;
(d) introducing to melt onto the vibrating casting plate to form melt droplets thereon;
(e) providing a cooling medium; and
(f) contacting the melt droplets with the cooling medium which is passed countercurrently to the melt droplets, thus forming the granular solids, and wherein the granular solids have a monodisperse particle size distribution and are substantially free of particles having a diameter of less than 0.3 mm.

12. The process of claim 11 wherein the one or more emulsifiers are nonionic surfactants selected from the group consisting of alkyl and/or alkenyl oligoglycosides, fatty acid N-alkyl-polyhydroxyalkylamides, fatty alcohol polyglycol ethers, mixed ethers, alkoxylated fatty acid alkyl esters, polyol poly-12-hydroxystearates, and mixtures thereof.

13. The process of claim 12 wherein at least one emulsifier is selected from a group consisting of one or more alkyl or alkenyl glycosides of formula (I)

$$R^1O\text{-}[G]_p \quad (I)$$

in which $R^1$ is an alkyl and/or alkenyl radical having 4 to 22 carbon atoms, G is a sugar radical having 5 or 6 carbon atoms and p is a number from 1 to 10, and polyglycerol poly-12-hydroxystearates.

14. The process of claim 13 wherein the alkyl or alkenyl glycosides of formula (I) are those in which $R^1$ is a linear or branched alkyl radical having 16 to 18 carbon atoms.

15. The process of claim 11 wherein the one or more wax bodies are selected from the group consisting of natural waxes, synthetic waxes, lecithins, phospholipids, pearlescent waxes, and mixtures thereof.

16. The process of claim 11 wherein the one or more bodying agents are selected from a group consisting of fatty alcohols and partial glycerides.

17. The process of claim 16 wherein at least one bodying agent is a fatty alcohol of formula (IV)

$$R^4OH \quad (IV)$$

in which $R^4$ is an aliphatic, linear or branched hydrocarbon radical having 6 to 22 carbon atoms and 0, 1, 2 or 3 double bonds.

18. The process of claim 17 wherein the at least one bodying agent of formula (IV) is selected from those in which $R^4$ is a linear or branched alkyl radical having 16 to 18 carbon atoms.

19. The process of claim 11 wherein the substantially anhydrous preparation contains less than 25% by weight water, based on the weight of the preparation.

20. The process of claim 11 wherein the vibrating casting plate vibrates at an oscillating frequency ranging from about 100 to 1000 Hz.

21. The process of claim 11 wherein the melt drops are contacted with the cooling medium in a drop-formation tower.

* * * * *